(12) United States Patent
Yavari et al.

(10) Patent No.: US 11,248,183 B2
(45) Date of Patent: Feb. 15, 2022

(54) COMPOSITION USEFUL AS FRICTION MODIFIER

(71) Applicant: OLEON NV, Evergem (BE)

(72) Inventors: Keihann Yavari, Margny-les-Compiegne (FR); Lieven Van Hecke, Kortrijk (BE); Scott A. Culley, Midlothian, VA (US); Charles Shanahan, Richmond, VA (US); Michel Nuckols, Midlothian, VA (US)

(73) Assignee: OLEON NV, Evergem (BE)

( * ) Notice: Subject to any disclaimer, the term of this patent is extended or adjusted under 35 U.S.C. 154(b) by 0 days.

(21) Appl. No.: 16/958,627

(22) PCT Filed: Dec. 26, 2018

(86) PCT No.: PCT/EP2018/086888
§ 371 (c)(1),
(2) Date: Jun. 26, 2020

(87) PCT Pub. No.: WO2019/129793
PCT Pub. Date: Jul. 4, 2019

(65) Prior Publication Data
US 2020/0332207 A1    Oct. 22, 2020

(30) Foreign Application Priority Data
Dec. 27, 2017  (EP) .................... 17210718

(51) Int. Cl.
*C10L 1/224* (2006.01)
*C07C 227/18* (2006.01)
*C07C 231/02* (2006.01)
*C10L 1/222* (2006.01)
*C10L 1/2387* (2006.01)
*C10L 10/08* (2006.01)
*C10M 105/60* (2006.01)
*C10M 105/68* (2006.01)

(52) U.S. Cl.
CPC ............ *C10L 1/224* (2013.01); *C07C 227/18* (2013.01); *C07C 231/02* (2013.01); *C10L 1/2225* (2013.01); *C10L 1/2387* (2013.01); *C10L 10/08* (2013.01); *C10M 105/60* (2013.01); *C10M 105/68* (2013.01); *C10L 2200/0423* (2013.01); *C10L 2230/14* (2013.01); *C10L 2230/22* (2013.01); *C10L 2270/023* (2013.01); *C10M 2215/265* (2013.01); *C10M 2215/285* (2013.01)

(58) Field of Classification Search
CPC ...... C10L 1/224; C10L 1/2225; C10L 1/2387; C10L 10/08; C10L 2200/0423; C10L 2230/14; C10L 2230/22; C10L 2270/023; C10M 105/60; C10M 105/68; C10M 2215/265; C10M 2215/285; C07C 227/18; C07C 231/02
See application file for complete search history.

(56) References Cited

U.S. PATENT DOCUMENTS

| 4,208,293 A | 6/1980 | Zaweski | |
| 4,729,769 A * | 3/1988 | Schlicht | C10L 1/224 44/418 |
| 6,743,266 B2 * | 6/2004 | DeRosa | C10L 1/143 44/347 |
| 2005/0107623 A1 | 5/2005 | Fox et al. | |
| 2010/0132253 A1 | 6/2010 | Kaufinan et al. | |

FOREIGN PATENT DOCUMENTS

| EP | 3144370 A1 | 3/2017 |
| GB | 2252555 A | 2/1991 |

OTHER PUBLICATIONS

International Search Report received in PCT/EP2018/086888, dated Mar. 22, 2019.

* cited by examiner

*Primary Examiner* — Cephia D Toomer
(74) *Attorney, Agent, or Firm* — Arent Fox LLP

(57) ABSTRACT

The present invention relates to the field of fuel additives for fuel compositions and more particularly to a composition that can be used as a friction modifier, and its preparation process. More particularly, the present invention concerns a composition comprising at least one fatty acid amide of diethanolamine (DEA) and at least one fatty acid ester and/or amide of DEA oligomer, and it preparation process.

14 Claims, No Drawings

COMPOSITION USEFUL AS FRICTION MODIFIER

This application is related to a co-pending application filed this same day as a result of a joint development between Oleon NV of Belgium, Oleon SAS of France and Afton Chemical Corporation of Richmond, Va., USA.

The present invention relates to the field of fuel additives for fuel compositions and more particularly to a composition that can be used as a friction modifier, and its preparation process.

Fuel compositions for vehicles are continually being improved to enhance various properties of the fuels in order to accommodate their use in newer, more advanced engines including direct injection gasoline engines. Accordingly, fuel compositions typically include additives that are directed to certain properties that require improvement. For example, friction modifiers are added to fuel to reduce friction and wear in the fuel delivery systems of an engine. In addition, special components may be added to fuel to reduce injector nozzle fouling, clean dirty injectors and improve the performance of direct injection combustion engines. When such additives are added to the fuel, a portion of the additives is transferred into the thin film of lubricant in the engine piston ring zone where it may also reduce friction and wear and thus improve fuel economy. Such fuel additives are passed into the crankcase during engine operation, so that a fuel additive that is also beneficial to the engine lubricant is desirable. However, fuel additive concentrates containing friction modifiers made from diethanolamine and certain fatty acids or their corresponding esters, may be unstable when stored at low temperatures and the performance of such friction modifiers is often less than desirable. In addition, certain fatty acid based amine and alkanolamide friction modifiers are waxes or partial solids that are difficult to handle at low ambient temperatures.

Friction modifiers that are made from acids and esters that are derived from saturated or mono-unsaturated fatty acids such as lauric, myristic, palmitic, and stearic acid are particularly difficult to formulate into additive concentrates that remain fluid and homogeneous at low temperatures. The instability can be exacerbated by the typical detergent additives that are used in fuel additive concentrates, such as polyisobutene Mannich additives. Since additive concentrates are the preferred form to blend fuel additive components into the fuel, it is essential that fuel additive concentrates be homogeneous and remain fluid at low temperatures, preferably down to about −20° C. or lower.

When the friction modifier additive concentration is fairly high in the concentrate, compatibilizers and/or large amounts of solvent may be added to the additive composition to improve its solubility at low temperatures. Compatibilizers that have been used include low molecular weight alcohols, esters, anhydrides, succinimides, glycol ethers, and alkylated phenols, and mixtures thereof. Alternatively, some additive producers have incorporated low molecular weight esters into the reaction mixture of fatty acids with the diethanolamine to enhance the low temperature stability of the reaction product. Unfortunately, the costs that solvents, compatibilizers, and low molecular weight esters add to additive concentrates may make their use uneconomical.

Partial esters of fatty acids and polyhydroxy alcohols such as glycerol monooleate (GMO) and fatty amine ethoxylates such as diethoxylated laurylamine are also known fuel additives that reduce friction and wear and may improve fuel economy. GMO and some fatty amine ethoxylates have poor compatibility in fuel additive concentrates when the compositions are stored at low temperatures. It is particularly difficult to prepare fuel additive concentrates containing both GMO and fatty amine diethoxylates that are stable at low temperature. While GMO and fatty amine ethoxylate friction modifiers may improve fuel economy when added to a fuel, GMO and certain fatty amine ethoxylates may be unstable in additive concentrates or may require large amounts of solvent and compatibilizers to keep the additive concentrate stable and fluid at low temperatures. Accordingly, GMO, fatty amine ethoxylates, and fatty alkanolamide friction modifiers cannot be beneficially added to a fuel composition to improve the fuel economy and wear protection of the fuel delivery system unless they can be formulated into a stable fuel additive concentrate.

Many other friction modifiers have been tried, however there remains a need for a friction modifier that can be readily formulated into fuel additive concentrates that are stable at low temperatures, i.e., temperatures as low as about −20° C. There is also a need for a friction modifier that improves the low temperature compatibility of other fuel additive components in fuel additive concentrates. Moreover, there is a need for a friction modifier that improves the friction and wear properties of other fuel additives. Additionally, there is a need for a friction modifier that improves fuel economy, and that provides wear protection to fuel delivery systems, among others characteristics.

Fuel compositions for direct fuel injected engines often produce undesirable deposits in the injectors, engine combustion chambers, fuel supply systems, fuel filters, and intake valves. Accordingly, improved compositions that can prevent deposit build up and maintain cleanliness "as new" for the life of the vehicle are desired. A composition that can clean dirty fuel injectors restoring performance to the previous "as new" condition and improve the power performance of the engines would be equally desirable and valuable in the attempt to reduce air borne exhaust emissions. Although there are additives known to reduce injector nozzle fouling and reduce intake valve deposits, their clean-up performance and keep clean effect may be insufficient. Furthermore, their stability and interaction with other fuel additives may be unsatisfactory. Accordingly, there continues to be a need for a fuel additive that is cost effective, readily incorporated into additive concentrates, and improves multiple characteristics of a fuel.

The work of the inventors has made it possible to demonstrate that a particular composition makes it possible to overcome the drawbacks mentioned above.

According to a first aspect, the invention relates to a composition comprising at least one fatty acid amide of diethanolamine (DEA) and at least one fatty acid ester and/or amide of DEA oligomer.

By "fatty acid amide of DEA", it is intended the amide resulting from the amidification reaction between a DEA and a fatty acid.

By "fatty acid ester of DEA oligomer", it is intended the ester resulting from the esterification reaction between a DEA oligomer and a fatty acid.

By "fatty acid amide of DEA oligomer", it is intended the amide resulting from the amidification reaction between a DEA oligomer and a fatty acid.

DEA is of formula (I):

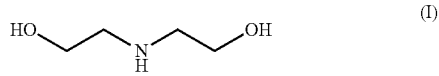

By "oligomer", it is intended a molecule comprising from 2 to 5 DEA monomers.

The composition according to the invention remains fluid at a temperature down to about 0° C., preferably, down to about −5° C., more preferably down to −20° C.

Advantageously, the fatty acid is linear and comprises from 8 to 18 carbon atoms, preferably from 12 to 16.

In the present application, unless otherwise indicated, all ranges of values used are to be understood as being inclusive limits.

Preferably, the fatty acid is saturated.

Preferably, the at least one fatty acid amide of DEA is N,N-bis(2-hydroxyethyl)alkylamide. Preferably, in the alkylamide, the alkyl group is linear and comprises from 8 to 18 carbon atoms.

Still more preferably, the at least one fatty acid amide of DEA is N,N-bis(2-hydroxyethyl)dodecanamide.

N,N-bis(2-hydroxyethyl)dodecanamide is of formula (II):

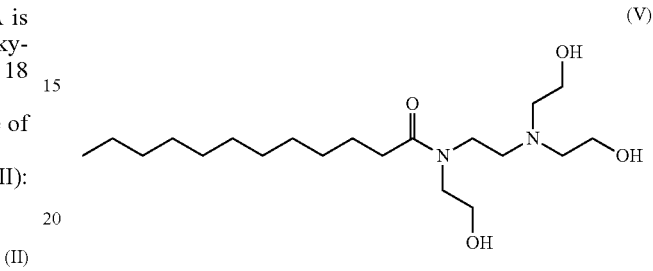

(II)

The composition according to the first aspect also comprises at least one fatty acid ester and/or amide of DEA oligomer.

Advantageously, the at least one fatty acid ester and/or amide of DEA oligomer is a fatty acid ester and/or amide of DEA dimer.

DEA dimer is of formula (III):

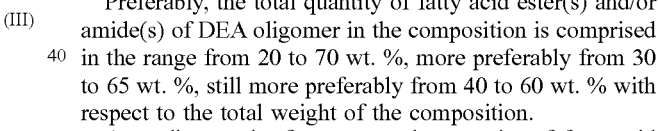

(III)

Preferably the at least one fatty acid ester of DEA dimer is 2-((2-(bis(2-hydroxyethyl)amino)ethyl)amino)ethylalkanoate. More preferably, in the ethylalkanoate, the alkyl group is linear and comprises from 8 to 18 carbon atoms.

Still more preferably the at least one fatty acid ester of DEA dimer is 2-((2-(bis(2-hydroxyethyl)amino)ethyl)amino)ethyldodecanoate.

2-((2-(bis(2-hydroxyethyl)amino)ethyl)amino)ethyldodecanoate is of formula (IV):

Preferably, the at least one fatty acid amide of DEA dimer is N-(2-(bis(2-hydroxyethyl)amino)ethyl)-N-(2-hydroxyethyl)alkylamide. More preferably, in the alkylamide, alkyl group is linear and comprises from 8 to 18 carbon atoms.

Still more preferably, the at least one fatty acid amide of DEA dimer is N-(2-(bis(2-hydroxyethyl)amino)ethyl)-N-(2-hydroxyethyl)dodecanamide.

N-(2-(bis(2-hydroxyethyl)amino)ethyl)-N-(2-hydroxyethyl)dodecanamide is of formula (V):

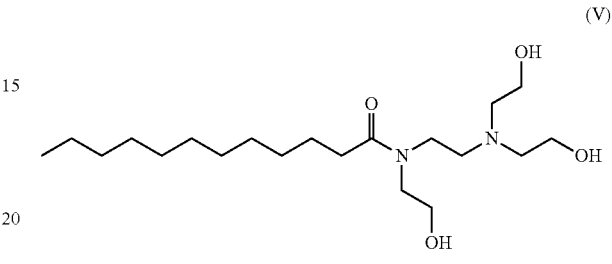

(V)

The at least one fatty acid ester and/or amide of DEA oligomer can also be a fatty acid ester and/or amide of DEA trimer.

According to the first aspect, the total quantity of fatty acid ester(s) and/or amide(s) of DEA oligomer in the composition is advantageously comprised in the range from 15 to 80 wt. % with respect to the total weight of the composition.

By "fatty acid ester(s) of DEA oligomer", it is intended all the ester(s) resulting from the esterification reaction between DEA oligomer(s) and fatty acid(s).

By "fatty acid amide(s) of DEA oligomer", it is intended all the amide(s) resulting from the amidification reaction between DEA oligomer(s) and fatty acid(s).

Preferably, the total quantity of fatty acid ester(s) and/or amide(s) of DEA oligomer in the composition is comprised in the range from 20 to 70 wt. %, more preferably from 30 to 65 wt. %, still more preferably from 40 to 60 wt. % with respect to the total weight of the composition.

According to the first aspect, the quantity of fatty acid ester(s) of DEA dimer and fatty acid amide(s) of DEA dimer in the composition is advantageously comprised in the range from 15 to 80 wt. % with respect to the total weight of the composition.

Preferably, the quantity of fatty acid ester(s) of DEA dimer and fatty acid amide(s) of DEA dimer in the composition is comprised in the range from 15 to 50 wt. %, more preferably from 25 to 45 wt. %, still more preferably from 30 to 40 wt. % with respect to the total weight of the composition.

Preferably, the composition comprises from 15 to 50 wt. % of 2-((2-(bis(2-hydroxyethyl)amino)ethyl)amino)ethylal-

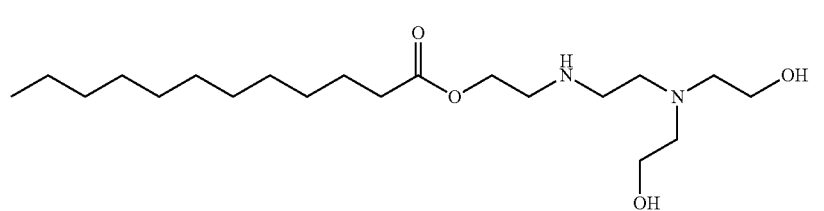

(IV)

kanoate and N-(2-(bis(2-hydroxyethyl)amino)ethyl)-N-(2-hydroxyethyl)alkylamide, more preferably from 25 to 45 wt. %, still more preferably from 30 to 40 wt. % with respect to the total weight of the composition.

The composition may advantageously comprise from 0.5 to 30 wt. % of fatty acid ester(s) and amide(s) of DEA oligomer other than fatty acid esters and amides of DEA dimers, such as fatty acid ester(s) and amide(s) of DEA trimer.

Preferably, the composition may comprise from 5 to 25 wt. %, more preferably from 10 to 20 wt. % of fatty acid ester(s) and amide(s) of DEA oligomer other than fatty acid esters and amides of DEA dimers with respect to the total weight of the composition. Advantageously, fatty acid ester(s) and amide(s) of DEA oligomer other than fatty acid esters and amides of DEA dimers, is/are fatty acid ester(s) and amide(s) of DEA trimer.

The composition according to the first aspect comprises less than 3 wt. % of BHEP (N,N'-bis(2-hydroxyethyl)piperazine), preferably less than 2 wt. %, more preferably less than 0.5 wt. %, still more preferably less than 0.2 wt. % with respect to the total weight of the composition.

According to the first aspect, the quantity of fatty acid amide(s) of DEA is advantageously comprised in the range from 20 to 85 wt. % with respect to the total weight of the composition.

Preferably, the quantity of fatty acid amide(s) of DEA is comprised in the range from 30 to 60 wt. %, more preferably from 40 to 55 wt. % with respect to the total weight of the composition.

Preferably, the composition comprises from 30 to 60 wt. %, more preferably from 40 to 55 wt. % of N,N-bis(2-hydroxyethyl)alkylamide, with respect to the total weight of the composition. Preferably, preferred compounds for alkylamide and N,N-bis(2-hydroxyethyl)alkylamide are as disclosed above.

The composition according to the first aspect comprises less than 15 wt. % of DEA, preferably less than 10 wt. %, more preferably less than 5 wt. %.

Advantageously, the composition according to the first aspect comprises less than 1 wt. % of DEA.

In one embodiment of the first aspect, the composition comprises:
30 to 60 wt. % of fatty acid amide(s) of diethanolamide;
25 to 45 wt. % of fatty acid ester(s) of DEA dimer and fatty acid amide(s) of DEA dimer;
5 to 25 wt. % of fatty acid ester(s) and amide(s) of DEA oligomer other than fatty acid esters and amides of DEA dimer.

In a preferred embodiment of the first aspect, the composition comprises:
40 to 55 wt. % of N,N-bis(2-hydroxyethyl)alkylamide,
30 to 40 wt. % of 2-((2-(bis(2-hydroxyethyl)amino)ethyl)amino)ethylalkanoate and N-(2-(bis(2-hydroxyethyl)amino)ethyl)-N-(2-hydroxyethyl)alkylamide, and
10 to 20 wt. % of fatty acid ester(s) and amide(s) of DEA oligomer other than fatty acid esters and amides of DEA dimer,
the wt. % being with respect to the total weight of the composition.

Preferably, preferred compounds for alkylamide, alkanoate, N,N-bis(2-hydroxyethyl)alkylamide, 2-((2-(bis(2-hydroxyethyl)amino)ethyl)amino)ethylalkanoate and N-(2-(bis(2-hydroxyethyl)amino)ethyl)-N-(2-hydroxyethyl)alkylamide are as disclosed above. In particular, at least 45 wt. % of the alkyl residues in the alkylamide and alkanoate comprise 12 carbon atoms. Similarly, at least 45 wt. % of the fatty acid residues in the fatty acid ester(s) and amide(s) of DEA oligomer comprise 12 carbon atoms.

The invention also relates to a process for preparing a composition according to the first aspect, by reacting fatty acid(s) with DEA, wherein the reaction is conducted in the presence of a molar excess of DEA relative to the fatty acid(s) and at a pressure below 50000 Pa, preferably from 10 to 50000 Pa, such as from 2000 to 50000 Pa (20 to 500 mBar).

All the quantities of reactants are directly placed in a reactor and can be reacted in one step.

Preferably, the pressure is from 10000 to 30000 Pa (100 to 300 mBar).

Alternatively, the pressure is below 10000 Pa, preferably below 5000 Pa.

Preferably, the molar excess of DEA is from 1.2 to 5 equivalents of DEA, more preferably from 1.5 to 4 equivalents of DEA.

Advantageously, in the process for preparing a composition according to the first aspect, the reaction is conducted at a temperature between 120 and 160° C.

Preferably, the reaction is conducted at a temperature between 130 and 150° C.

No alkaline catalyst is needed to perform the reaction. On the contrary, if any, an acid catalyst may be used.

In the process for preparing a composition according to the first aspect, the reaction time is of about 6 to 30 h, preferably, 10 to 26 h.

The process for preparing a composition according to the first aspect, can be conducted in two steps:
a first step wherein the reaction is conducted at a pressure from above 5000 to 50000 Pa (50 to 500 mBar) to obtain a reaction mixture, and,
once the reaction mixture reached an acid value of 50, a second step wherein the pressure is reduced to a pressure from 1000 to 5000 Pa (10 to 50 mBar).

This further reduction of the pressure allows removing water and displacing the reaction equilibrium towards the ester(s)/amide(s) formation.

Alternatively, the process for preparing a composition according to the first aspect, can be conducted in one step, wherein the reaction is conducted at a pressure below 50000 Pa (500 mBar), preferably below 30000 Pa, more preferably below 10000 Pa, still more preferably below 5000 Pa. In the process for preparing a composition according to the first aspect, the fatty acid(s) is advantageously lauric acid, myristic acid, capric acid and/or caprylic acid.

Lauric acid is a 12 carbon chain fatty acid, myristic acid is a 14 carbon chain fatty acid, capric acid is a 10 carbon chain fatty acid and caprylic acid is a 8 carbon chain fatty acid.

Preferably, the fatty acid(s) is lauric acid.

Preferably, the fatty acid(s) are fatty acids resulting from coconut oil. As an example, fatty acids can result from hydrolyzation of coconut oil. Once hydrolyzed, the resulting mixture of fatty acids is particularly rich in lauric acid.

Advantageously, the excess of DEA is removed after the reaction is completed.

It is considered that the reaction is completed when the acid value of the reaction mixture is below 5, preferably, below 3, more preferably below 2. The acid value can be measured according to standard AOCS Cd 3D-63.

Preferably, once the reaction is completed, the excess of DEA and optionally fatty acid(s) is removed, preferably by distillation. This also allows the obtained composition according to the first aspect to have a BHEP content of less than 0.5 wt. %, preferably less than 0.2 wt. % with respect to the total weight of the composition.

In a second aspect, the invention also relates to a composition comprising at least two compounds selected from the group consisting of fatty acid esters of diethanolamine (DEA) oligomer and fatty acid amides of diethanolamine (DEA) oligomer.

Said composition preferably comprises at least one fatty acid ester and/or amide of DEA dimer.

More preferably, the at least one fatty acid ester of DEA dimer is 2-((2-(bis(2-hydroxyethyl)amino)ethyl)amino)ethylalkanoate and/or the at least one fatty acid amide of DEA dimer is N-(2-(bis(2-hydroxyethyl)amino)ethyl)-N-(2-hydroxyethyl)alkylamide.

Still more preferably, the at least one fatty acid ester of DEA dimer is 2-((2-(bis(2-hydroxyethyl)amino)ethyl)amino)ethyldodecanoate and/or the at least one fatty acid amide of DEA dimer is N-(2-(bis(2-hydroxyethyl)amino)ethyl)-N-(2-hydroxyethyl)dodecanamide.

The composition according to the second aspect further comprises a fatty acid amide of DEA. Preferably, the fatty acid amide of DEA is N,N-bis(2-hydroxyethyl)alkylamide, more preferably, the fatty acid amide of DEA is N,N-bis(2-hydroxyethyl)dodecanamide.

The composition according to the second aspect may further comprise a fatty acid ester and/or amide of DEA trimer.

In the composition according to the second aspect, the total quantity of fatty acid ester(s) and amide(s) of DEA oligomer is comprised in the range from 15 to 80 wt. %, preferably from 20 to 70 wt. %, more preferably from 30 to 65 wt. %, still more preferably from 40 to 60 wt. % with respect to the total weight of the composition.

More particularly, the total quantity of fatty acid ester(s) and amide(s) of DEA dimer is comprised in the range from 15 to 80 wt. %, preferably from 25 to 45 wt. %, more preferably from 30 to 40 wt. % with respect to the total weight of the composition.

Still more preferably, the composition comprises from 15 to 50 wt. % of 2-((2-(bis(2-hydroxyethyl)amino)ethyl)amino)ethylalkanoate and N-(2-(bis(2-hydroxyethyl)amino)ethyl)-N-(2-hydroxyethyl)alkylamide, more preferably from 25 to 45 wt. %, still more preferably from 30 to 40 wt. % with respect to the total weight of the composition.

The composition according to the second aspect may advantageously comprise from 0.5 to 30 wt. %, preferably from 5 to 25 wt. %, more preferably from 10 to 20 wt. % of fatty acid ester(s) and amide(s) of DEA oligomer other than fatty acid esters and amides of DEA dimer, such as fatty acid ester(s) and amide(s) of DEA trimer.

The composition according to the second aspect comprises less than 3 wt. % of BHEP (N,N'-bis(2-hydroxyethyl)piperazine), preferably less than 2 wt. %, more preferably less than 0.5 wt. %, still more preferably less than 0.2 wt. % with respect to the total weight of the composition.

In the composition according to the second aspect, the quantity of fatty acid amide(s) of DEA is comprised in the range from 20 to 85 wt. %, preferably from 30 to 60 wt. %, more preferably from 40 to 55 wt. % with respect to the total weight of the composition.

Advantageously, the composition according to the second aspect comprises at least 20 wt. %, more preferably at least 25 wt. % of N,N-bis(2-hydroxyethyl)alkylamide. Preferably the N,N-bis(2-hydroxyethyl)alkylamide is N,N-bis(2-hydroxyethyl)dodecanamide.

In a third aspect, the invention also relates to a fatty acid ester of diethanolamine (DEA) oligomer.

Preferably, said ester is a fatty acid ester of DEA dimer and more particularly 2-((2-(bis(2-hydroxyethyl)amino)ethyl)amino)ethylalkanoate, and more particularly 2-((2-(bis(2-hydroxyethyl)amino)ethyl)amino)ethyldodecanoate.

In this third aspect, the invention further relates to a composition comprising said fatty acid ester of DEA oligomer. More particularly, the composition according to the third aspect comprises at least one fatty acid ester of DEA oligomer according to the third aspect, and at least one fatty acid ester or amide of DEA and/or at least one fatty acid amide of DEA oligomer and/or at least a second fatty acid ester of DEA oligomer.

Preferably the at least one fatty acid amide of DEA oligomer is a fatty acid amide of DEA dimer, and more particularly is N-(2-(bis(2-hydroxyethyl)amino)ethyl)-N-(2-hydroxyethyl)alkylamide, still more particularly N-(2-(bis(2-hydroxyethyl)amino)ethyl)-N-(2-hydroxyethyl)dodecanamide.

In the composition according to the third aspect, the at least one fatty acid amide of DEA is N,N-bis(2-hydroxyethyl)alkylamide, more preferably N,N-bis(2-hydroxyethyl)dodecanamide.

Advantageously, the second fatty acid ester of DEA oligomer is a fatty acid ester of DEA trimer.

In the composition according to the third aspect, the total quantity of fatty acid ester(s) and/or amide(s) of DEA oligomer is comprised in the range from 15 to 80 wt. %, preferably from 20 to 70 wt. %, more preferably from 30 to 65 wt. %, still more preferably from 40 to 60 wt. % with respect to the total weight of the composition.

In the composition according to the third aspect, the quantity of fatty acid ester(s) of DEA dimer and fatty acid amide(s) of DEA dimer is comprised in the range from 15 to 80 wt. %, preferably from 15 to 50 wt. %, more preferably from 25 to 45 wt. %, still more preferably from 30 to 40 wt. % with respect to the total weight of the composition.

The composition according to the third aspect may advantageously comprise from 0.5 to 30 wt. %, preferably from 5 to 25 wt. %, more preferably from 10 to 20 wt. % of fatty acid ester(s) and amide(s) of DEA oligomer other than fatty acid esters and amides of DEA dimer, such as fatty acid ester(s) and amide(s) of DEA trimer.

The composition according to the third aspect comprises less than 3 wt. % of BHEP (N,N'-bis(2-hydroxyethyl)piperazine), preferably less than 2 wt. %, more preferably less than 0.5 wt. %, still more preferably less than 0.2 wt. % with respect to the total weight of the composition.

In the composition according to the third aspect, the quantity of fatty acid amide of DEA is comprised in the range from 20 to 85 wt. %, preferably from 30 to 60 wt. %, more preferably from 40 to 55 wt. % with respect to the total weight of the composition.

Advantageously, the composition according to the third aspect comprises at least 20 wt. %, more preferably, at least 25 wt. % of N,N-bis(2-hydroxyethyl)alkylamide. Preferably the N,N-bis(2-hydroxyethyl)alkylamide is N,N-bis(2-hydroxyethyl)dodecanamide.

Preferably, in the second and third aspects of the invention, preferred compounds for alkylamide, alkanoate, N,N-bis(2-hydroxyethyl)alkylamide, 2-((2-(bis(2-hydroxyethyl)amino)ethyl)amino)ethylalkanoate and N-(2-(bis(2-hydroxyethyl)amino)ethyl)-N-(2-hydroxyethyl)alkylamide are as disclosed in the first aspect. In particular, at least 45 wt. % of the alkyl residues in the alkylamide and alkanoate comprise 12 carbon atoms. Similarly, at least 45 wt. % of the fatty acid residues in the fatty acid ester(s) and amide(s) of DEA oligomer comprise 12 carbon atoms.

The invention is further described in the following examples. It will be appreciated that the invention as claimed is not intended to be limited in any way by these examples.

EXAMPLE 1: PREPARATION OF A COMPOSITION ACCORDING TO THE INVENTION

1. Material

1.1. Fatty Acids

Radiacid® 0628 from OLEON was used. This product is composed of C8-C18 fatty acids from coconut oil.

It is notably composed of from 45 to 56 wt. % of lauric acid, and from 15 to 23 wt. % of myristic acid.

Acid value: 264-277 mg KOH/g, measured according to standard AOCS Cd 3D-63.

Calculated iodine number: 6-15

1.2. DEA

Diethalolamine from Helm was used (CAS: 111-42-2). This product is composed of more than 98.5 wt. % of DEA, less than 1.3 wt. % methylethanolamine (MEA) and less than 1 wt. % of triethanolamine (TEA).

Melting point: 27° C.
Boiling point: 270° C.

2. Methods

2.1. Preparation of Composition 1 According to the Invention

In a reactor, 4.0 mol of Radiacid® 0628 and 8.0 mol of DEA (2 equivalents) were introduced at the same time. Progressively, the reaction mixture was brought to 150° C. with stirring and the pressure was reduced to 20000 Pa (200 mBar) for about 10 hours. Once acid value reached 50 mg KOH/g, the pressure was reduced to 2000 Pa (20 mBar) until acid value became smaller than 2 mg KOH/g. Then, the reaction product mixture was distilled to remove excess of DEA and optionally fatty acid(s). Spectroscopy of the material showed a 8.9:1 ratio of amide absorbance at 1622 $cm^{-1}$ to ester absorbance at 1740 $cm^{-1}$.

Identification of the compounds in the resulting composition was determined by GC-MS and quantification of compounds by GC-FID.

The composition according to the invention comprises:
- 47 wt. % of N,N-bis(2-hydroxyethyl)alkylamides, wherein the alkyl group comprises from 8 to 18 carbon atoms;
- 33 wt. % of 2-((2-(bis(2-hydroxyethyl)amino)ethyl)amino)ethylalkanoates and N-(2-(bis(2-hydroxyethyl)amino)ethyl)-N-(2-hydroxyethyl)alkylamides, wherein the alkyl groups comprise from 8 to 18 carbon atoms; and
- 16 wt. % of fatty acid esters and amides of DEA trimer, wherein fatty acids comprise from 8 to 18 carbon atoms;

the wt. % being with respect to the total weight of the composition.

In the following Example, it is intended:
- by Coco-DEA: N,N-bis(2-hydroxyethyl)alkylamides, wherein the alkyl group comprises from 8 to 18 carbon atoms;
- by Coco-(DEA dimer) (DEA dimer being the self-condensation products of DEA): 2-((2-(bis(2-hydroxyethyl)amino)ethyl)amino)ethylalkanoates and N-(2-(bis(2-hydroxyethyl)amino)ethyl)-N-(2-hydroxyethyl)alkylamides, wherein the alkyl groups comprise from 8 to 18 carbon atoms.

2.2 Preparation of Composition 2 According to the Invention

In a reactor, 4.0 mol of Radiacid® 0628 and 8.0 mol of DEA (2 equivalents) were introduced at the same time. Progressively, the reaction mixture was brought to 135° C. with stirring and the pressure was reduced to 2000 Pa (20 mBar) for about 10 hours. Once acid value became smaller than 2 mg KOH/g, the reaction product mixture was distilled to remove excess of DEA and optionally fatty acid(s).

The composition according to the invention comprises:
- 42 wt. % of N,N-bis(2-hydroxyethyl)alkylamides, wherein the alkyl group comprises from 8 to 18 carbon atoms;
- 34 wt. % of 2-((2-(bis(2-hydroxyethyl)amino)ethyl)amino)ethylalkanoates and N-(2-(bis(2-hydroxyethyl)amino)ethyl)-N-(2-hydroxyethyl)alkylamides, wherein the alkyl groups comprise from 8 to 18 carbon atoms; and
- 19 wt. % of fatty acid esters and amides of DEA trimer, wherein fatty acids comprise from 8 to 18 carbon atoms;

the wt. % being with respect to the total weight of the composition.

EXAMPLE 2: TEMPERATURE STORAGE STABILITY OF THE COMPOSITION ACCORDING TO THE INVENTION AND COMPARATIVES COMPOSITIONS

Low temperature storage stability tests of gasoline fuel additive concentrates containing the composition according to the invention were compared to those of gasoline fuel additive concentrates containing either Coco-DEA or Coco-DEA with addition a given percentage of Coco-(DEA dimer) as mentioned in Table 1 below.

The Coco-DEA was made by amidation between coconut fatty acids and DEA and purified to remove any products derived from DEA dimers, trimers and higher oligomers. Likewise, the Coco-(DEA dimer) was made from coconut fatty acids and DEA and purified to remove any Coco-DEA and products derived from DEA trimers and higher oligomers. Each of the additive concentrates in the following table contained the same additive mixture treat rate. Indeed, the combined treat rate of the Coco-DEA and Coco-(DEA dimer) as well as the treat rate of the composition according to the invention was 20 wt. %.

Each of the gasoline fuel additive concentrates contained commonly used Mannich detergent, an aromatic solvent, C8 branched alcohol, carrier fluids, corrosion inhibitors, demulsifiers, and the like, besides the 20 wt. % of the additive mixture listed in Table 1 below.

Approximately 10 grams of each gasoline fuel additive concentrate was placed in a glass vial and stored at −20° C. for 28 days. The vials were visually inspected after 7 and 28 days and rated. The results are shown in Table 1 below.

TABLE 1

Temperature storage stability of gasoline fuel additive concentrates containing the composition according to the invention or comparative compositions

| Additive mixture | | | |
|---|---|---|---|
| Coco-DEA (wt. %) | Coco-(DEA dimer) (wt. %) | 7 days at −20° C. | 28 days at −20° C. |
| 100 | 0 | Heavy sediment | Solid |
| 95 | 5 | Heavy sediment | Solid |
| 90 | 10 | Heavy sediment | Heavy sediment |
| 85 | 15 | Light sediment | Heavy sediment |
| 80 | 20 | CB | Light sediment |
| 75 | 25 | CB | Light sediment |
| Composition according to the invention | | CB | CB |

By "stable" and "stability", it is meant the additive concentrate remains a clear fluid that is substantially free of sediment or precipitate and completely free of suspended matter, flocculent, and phase separation at temperatures as low as about −20° C. over a period of time. Samples that are clear and bright (CB) or have a light sediment layer not greater than 2 mm (light sediment) are considered to be acceptable.

These results evidenced the effect of the Coco-(DEA dimer). Above wt. 15% of Coco-(DEA dimer) in the additive mixture, it can be observed that the gasoline fuel additive concentrate is clear and bright at day 7 where Coco-DEA is already showing heavy sediment (at 15 wt. % of Coco-(DEA dimer) in the mixture, light sediment is observed).

At 28 days, use of an additive mixture with 20 wt. % of Coco-(DEA dimer) shows light sediment where lower ratio of Coco-(DEA dimer) shows heavy sediment or even solid solution at 0 wt. % and 5 wt. %. Only the composition according to the invention is still clear and bright at 28 days.

In all case, the composition according to the invention performs better than Coco-(DEA dimer), since in addition to Coco-(DEA dimer), it also contains ester/amides of trimers and other oligomers of DEA that enhance the properties at cold temperature.

EXAMPLE 3: PHYSICAL AND CHEMICAL PROPERTIES OF A COMPOSITION ACCORDING TO THE INVENTION AND OF COMPARATIVE COMPOSITIONS

Comparative Composition 1

Comparative composition 1 was prepared by heating 2.7 moles of Radiacid® 0628 and a calculated iodine number of 6-15 and 1.0 mole of diethanolamine (DEA) at 150° C. with stirring, in a small amount of xylene for approximately three hours and removing the water that is formed azeotropically. The reaction product contained as a major component C8-C18 fatty acid diesters and triesters of N,N-bis(2-hydroxyethyl)alkylamides. In a second step, 1.6 moles of diethanolamine were added to the N,N-bis(2-hydroxyethyl) alkylamide ester mixture that was obtained in the first step and the mixture was heated to 150° C. with stirring for approximately two hours after which the solvent was distilled off to give a brown viscous oil. The progress of the reaction was monitored by removing aliquots and measuring the amide:ester ratio by infrared spectroscopy. Transmission Infrared Spectroscopy of the material showed a 2.9:1 ratio of amide absorbance at 1622 $cm^{-1}$ to ester absorbance at 1740 $cm^{-1}$. Comparative composition 1 is further described in Table 2 below.

Comparative Composition 2

Comparative composition 2 was prepared in a single step by mixing 1.0 moles of DEA with 1.1 moles of Radiacid® 0628. A small amount of xylene was added and the mixture was heated to 150° C. with stirring and the water was removed azeotropically. Using a slight excess of fatty acid ensures that there is a minimal amount of unreacted diethanolamine at the end of the reaction. The progress of the reaction was monitored by removing aliquots and measuring the amide:ester ratio by infrared spectroscopy. Transmission Infrared Spectroscopy of the material showed a 2.3:1 ratio of amide absorbance at 1622 $cm^{-1}$ to ester absorbance at 1740 $cm^{-1}$. Comparative composition 2 is further described in Table 2 below.

Comparative Composition 3

Comparative composition 3 was prepared in the same manner as Comparative composition 2, but used isostearic acid having an acid value of 180 to 205 mg KOH/g and a calculated iodine number of below 4 instead of coconut fatty acid and employed a molar ratio of isostearic acid to diethanolamine of 1.4:1. Spectroscopy of the material showed a 1.1:1 ratio of amide absorbance at 1622 $cm^{-1}$ to ester absorbance at 1740 $cm^{-1}$. Comparative composition 3 is further described in Table 2 below.

Composition 1 According to the Invention

The composition 1 according to the invention is prepared as mentioned in Example 1. This composition is further described in Table 2 below.

TABLE 2

Physical and chemical properties of the composition according to the invention and of the comparative compositions.

| Example | BHEP (wt. %) | Free DEA (wt. %) | Nitrogen (wt. %) | TAN (mg KOH/g) | TBN (mg KOH/g) | PP (° C.) |
|---|---|---|---|---|---|---|
| Composition 1 according to the invention | <0.20 | <0.4 | 6.29 | 0.5 | 99.6 | −9 |
| Comparative composition 1 | 0.32 | 1.24 | 4.37 | 3.1 | 20.5 | +3 |
| Comparative composition 2 | 0.51 | 0.18 | 4.57 | 1.4 | 51.4 | −2 |
| Comparative composition 3 | 0.06 | 0.3 | 2.81 | 1.7 | 14.6 | <−30 |

The pour point (PP) data in Table 2 shows that the composition according to the invention had a lower pour point than both Comparative composition 1 (3° C.) and Comparative composition 2 (−2° C.). The pour point of the composition according to the invention is −9° C. when fatty acids derived from coconut oil are used.

When pure lauric acid is used instead of C8-C18 fatty acids from coconut oil to prepare the composition according to the invention, a pour point of −15° C. is observed and the pour point goes down to −34° C. when using pure caprylic acid. It is well known to one skilled in the art that shorter fatty acid chains result in better cold flow properties. Coconut oil possesses some palmitic and stearic acid, which increases the pour point whereas caprylic acid (C8) has a shorter hydrocarbon chain than lauric acid (C12). It was surprising and unexpected that the pour point of the composition according to the invention would be lower than the comparable compositions 1 and 2 when all three additives use the same fatty acid to make the additive.

The total base number (TBN) is defined as the quantity of acid expressed in terms of equivalent number of milligrams of potassium hydroxide that is required to neutralize all basic constituents present in 1 g of sample. This value was measured according to standard ASTM D2896-03. The higher the composition's TBN, the higher the number of nitrogen, meaning, more oligomers are present in the composition. The TBN of the composition 1 and 2 according to the invention are respectfully of 99.6 and 107, which are much higher than the TBN of comparative compositions, confirming the not negligible presence of DEA oligomers.

The total acid number (TAN) is defined as the quantity of milligrams of potassium hydroxide that is required to neutralize all acid constituents present in 1 g of sample. This value was measured according to standard AOCS Cd 3d-63.

EXAMPLE 4: WEAR PROPERTIES OF FUEL ADDITIVE CONCENTRATES COMPRISING A COMPOSITION ACCORDING TO THE INVENTION OR A COMPARATIVE COMPOSITION

In the following Fuel additive concentrates in Table 3, a wear test was conducted on an E10 gasoline fuel (base fuel). All of the Fuel additive concentrates contained E10 gasoline and the amount of composition listed in the table. Gasoline Packages 1 and 2 were two different conventional gasoline additive packages that contained Mannich detergents, carrier fluids, corrosion inhibitors, demulsifiers, and the like, plus solvent and a minor amount of 2-ethylhexanol. The wear tests were conducted using a high frequency reciprocating rig (HFRR) using method ASTM D 6079 that was modified to allow testing the gasoline at a temperature of 25° C. The average of two tests was used to determine the mean wear scar diameter (MWSD) results that are reported in Table 3.

TABLE 3

HFRR of fuel additive concentrates comprising a composition according to the invention or a comparative composition

| Fuel additive concentrate No. | Additive | Treat rate, ppm by wt. | HFRR Average MWSD (μm) |
| --- | --- | --- | --- |
| 1 | No additive: E10 gasoline only (base fuel) | 0 | 785 |
| 2 | Gasoline Package 1 | 304 | 768 |
| 3 | Composition 1 according to the invention plus Package 1 | 457 | 685 |
| 4 | Comparative composition 1 plus Package 1 | 457 | 753 |
| 5 | Comparative composition 2 plus Package 1 | 457 | 707 |
| 6 | Comparative composition 3 plus Package 1 | 457 | 744 |
| 7 | Gasoline Package 2 | 285 | 758 |
| 8 | Composition 1 according to the invention plus Package 2 | 438 | 602 |
| 9 | Comparative composition 1 plus Package 2 | 438 | 692 |
| 10 | Comparative composition 2 plus Package 2 | 438 | 674 |
| 11 | Comparative composition 3 plus Package 2 | 438 | 688 |

Fuel additive concentrates Nos. 1, 2, and 7 in Table 3 provide the HFRR data for the base fuel and the base fuel plus the two Gasoline Package concentrates respectively. The HFRR results for the base fuel plus concentrates with the composition 1 according to the invention (Fuel additive concentrates Nos. 3 and 8) were better than the comparative fuel additives (Fuel additive concentrates Nos. 4, 5, 6 and 9, 10, 11). The composition 1 according to the invention gave the lowest wear scar in both of the fuel additive concentrates. Fuel additive concentrates Nos. 4, 5, and 6 that contained Package 1 and comparative compositions 1, 2 and 3 respectively had HFRR wear scars above 700 microns while the Fuel additive concentrate No. 3 that contained the composition according to the invention had a wear scar of 685 microns. When Gasoline Package 2 was used, Fuel additive concentrate No. 8 containing the composition according to the invention had a wear scar of just over 600 microns while the fuel additive concentrates Nos. 9, 10, and 11 had wear scars of greater than of 670 microns. Accordingly, it was surprising and quite unexpected that the composition according to the invention would provide lower HFRR wear scars than the Fuel additive concentrates containing the comparative compositions. The lower wear scars of the Fuel additive concentrate containing composition 1 according to the invention could not be predicted from the data of Fuel additive concentrates Nos. 4-6 and 9-11.

EXAMPLE 5: WEAR PROPERTIES OF FUEL ADDITIVE CONCENTRATES COMPRISING THE COMPOSITION ACCORDING TO THE INVENTION WITH OTHER FRICTION MODIFIERS

This Example was conducted similarly to Example 4.

Gasoline Package 3 was a conventional gasoline additive packages that contained Mannich detergents, carrier fluids, corrosion inhibitors, demulsifiers, and the like, plus solvent and a minor amount of 2-ethylhexanol.

Comparative Composition 4

Comparative composition 4 was prepared by the method of U.S. Pat. No. 6,524,353 B2 which discloses a fuel additive composition consisting of the reaction product of (a) diethanolamine; (b) coconut oil; and (c) methyl caprylate; wherein the molar ratio of a:b:c: is 1.0:0.7:0.3.

Table 4 below provides the HFRR data for Fuel additive concentrates containing the composition according to the invention (Fuel additive concentrate No. 3'); the composition according to the invention with glycerol monooleate (GMO) (Fuel additive concentrate Nos. 14 and 15); and the composition according to the invention with fatty amine diethoxylate (diethoxylated laurylamine) (Fuel additive concentrate Nos. 16 and 17). The HFRR data for a fuel additive concentrate containing the composition according to the invention and both GMO and the fatty amine diethoxylate is also shown in Fuel additive concentrate No. 19.

Table 4 also provides the HFRR data for comparative composition 4, GMO, and diethoxylated laurylamine.

The composition according to the invention had a lower HFRR wear scar (575 microns) than either Comparative composition 4 (580), GMO (600) or diethoxylated lauryl amine (668) when tested at equal treat rate. It was surprising that the combination of the composition according to the invention and GMO gave a lower wear scar (566) than either component alone. The combination of the composition according to the invention with diethoxylated lauryl amine gave a lower wear scar (635) than diethoxylated laurylamine. In addition, when a small amount of the composition according to the invention was added to the additive concentrate containing both GMO and diethoxylated lauryl amine (No. 19) the resulting wear scar was better than GMO alone and the fatty aminediethoxylates alone.

TABLE 4

HFRR of fuel additive concentrates comprising a composition according to the invention with other FMs

| Fuel additive concentrate No. | Gasoline Package 3 | Composition 1 according to the invention | Comparative composition 4 | GMO | Diethoxylated lauryl-amine | Average MWSD (μm) |
|---|---|---|---|---|---|---|
| 1' | 0 | 0 | 0 | 0 | 0 | 741 |
| 2' | 304 | 0 | 0 | 0 | 0 | 704 |
| 3' | 304 | 153 | 0 | 0 | 0 | 575 |
| 12 | 304 | 0 | 153 | 0 | 0 | 580 |
| 13 | 304 | 0 | 0 | 153 | 0 | 600 |
| 14 | 304 | 76 | 0 | 76 | 0 | 566 |
| 15 | 304 | 153 | 0 | 153 | 0 | 520 |
| 16 | 304 | 76 | 0 | 0 | 76 | 635 |
| 17 | 304 | 153 | 0 | 0 | 153 | 639 |
| 18 | 304 | 0 | 0 | 0 | 153 | 668 |
| 19 | 304 | 38 | 0 | 76 | 76 | 598 |
| 20 | 304 | 0 | 0 | 76 | 76 | 629 |

EXAMPLE 6: USE OF THE COMPOSITION ACCORDING TO THE INVENTION AS A FRICTION MODIFIER

In the following Table 5, friction tests were conducted on SAE 0W-20 passenger car engine oil containing all of the standard engine oil components, but without friction modifiers. The treat rate of the composition according to invention or the comparative composition was 0.25 wt. % in the engine oil. The friction tests were conducted using a high frequency reciprocating rig (HFRR) under a 4 N load with a stroke distance of 1 millimeter at 20 Hz and a temperature of 130° C. The friction results are provided in Table 5.

TABLE 5

HFRR coefficient of engine oil comprising the composition according to the invention or comparative compositions.

| Engine oil No. | | Coefficient of Friction |
|---|---|---|
| 1 | Baseline Engine oil | 0.146 |
| 2 | Baseline oil with Comparative composition 1 | 0.120 |
| 3 | Baseline oil with Comparative composition 2 | 0.117 |
| 4 | Baseline oil with Comparative composition 3 | 0.134 |
| 5 | Baseline oil with Comparative composition 4 | 0.120 |
| 6 | Baseline oil with composition 1 according to the invention | 0.118 |

Table 5 provides the HFRR friction for the composition 1 according to the invention and comparative compositions (Engine oil Nos. 2-6) in a formulated engine oil without friction modifiers. In this case, the composition 1 according to the invention (Engine oil No. 6) provided a significant reduction in friction compared to the baseline oil (Engine oil No. 1). The composition 1 according to the invention (Engine oil No. 6) and the comparative compositions (Engine oil Nos. 2-5) gave similar coefficients of friction and all were better than the comparative composition 3 (Engine oil No. 4).

EXAMPLE 7: STABILITY OF THE COMPOSITION ACCORDING TO THE INVENTION AND COMPARATIVE COMPOSITIONS

An important characteristic of the composition according to the invention is its stability in fuel additive concentrates ("FAC") at low temperatures. Accordingly, in order to provide sufficient additive to a fuel to improve the wear in the fuel delivery system as well as the increasing the fuel economy of an engine, the additive concentrate containing the foregoing composition according to the invention must be stable and remain stable at low temperatures for an extended period in order to be useful as a fuel additive. It would also be very advantageous if the composition according to the invention could improve the stability of fuel additive concentrates containing fatty amine ethoxylates or partial esters of fatty acids or both at low temperatures.

In the following examples, the low temperature storage stability of gasoline fuel additive concentrates containing the composition 1 according to the invention ("Compo Invention") were compared to gasoline fuel additive concentrates containing the Comparative compositions ("Comp. compo") 1-4. Table 6 also contains stability data on fuel additive concentrates containing GMO and diethoxylated lauryl amine ("FAE").

Each of the additive concentrates in the following table contained 28.9 wt. % of a commonly used Mannich detergent, 19.9 wt. % of an aromatic solvent, 1.1 wt. % of a C8 branched alcohol, carrier fluids, corrosion inhibitors, demulsifiers, and the like. The total treat rate of the components other than the composition according to the invention and additional solvent was 67.3 wt. %.

Approximately 10 grams of each additive concentrate was placed in a glass vial and stored at −20° C. for 28 days. The vials were visually inspected after 14 and 28 days and rated. The results are shown in Table 6 below. The amount of composition (according to the invention or comparative) and additional solvent (95:5 wt. ratio of aromatic: C8 branched alcohol) in each of the examples is given in Table 6 below. All amounts are given in weight percent.

TABLE 6

Compatibility data

| FAC No. | Compo. Invention | Comp. Compo 1 | Comp. Compo 2 | Comp. Compo 3 | Comp. Compo 4 | GMO | FAE | Solvent | Four weeks at −20° C. |
|---|---|---|---|---|---|---|---|---|---|
| 1 | 15 | 0 | 0 | 0 | 0 | 0 | 0 | 17.7 | CB |
| 2 | 0 | 10 | 0 | 0 | 0 | 0 | 0 | 22.7 | Heavy Sediment |
| 3 | 0 | 0 | 10 | 0 | 0 | 0 | 0 | 22.7 | Heavy Sediment |
| 4 | 0 | 0 | 0 | 15 | 0 | 0 | 0 | 17.7 | CB |
| 5 | 0 | 0 | 0 | 0 | 15 | 0 | 0 | 17.7 | Medium Sediment |
| 6 | 0 | 0 | 0 | 0 | 10 | 0 | 0 | 22.7 | Light Sediment |

TABLE 6-continued

Compatibility data

| | | | | | | | | | |
|---|---|---|---|---|---|---|---|---|---|
| 7 | 0 | 0 | 0 | 0 | 0 | 5 | 0 | 27.7 | Medium Sediment |
| 8 | 5 | 0 | 0 | 0 | 0 | 5 | 0 | 22.7 | Light Sediment |
| 9 | 10 | 0 | 0 | 0 | 0 | 5 | 0 | 17.7 | CB |
| 10 | 0 | 10 | 0 | 0 | 0 | 5 | 0 | 17.7 | Heavy Sediment |
| 11 | 0 | 0 | 10 | 0 | 0 | 5 | 0 | 17.7 | Heavy Sediment |
| 12 | 0 | 0 | 0 | 10 | 0 | 5 | 0 | 17.7 | CB |
| 13 | 0 | 0 | 0 | 0 | 0 | 5 | 10 | 17.7 | CB |
| 14 | 0 | 0 | 0 | 0 | 0 | 0 | 10 | 22.7 | CB |
| 15 | 10 | 0 | 0 | 0 | 0 | 0 | 10 | 12.7 | CB |
| 16 | 0 | 10 | 0 | 0 | 0 | 0 | 10 | 12.7 | Heavy Sediment |
| 17 | 0 | 0 | 10 | 0 | 0 | 0 | 10 | 12.7 | Heavy Sediment |
| 18 | 0 | 0 | 0 | 10 | 0 | 0 | 10 | 12.7 | CB |
| 19 | 0 | 0 | 0 | 0 | 0 | 0 | 17.5 | 15.2 | Solid |
| 20 | 2.5 | 0 | 0 | 0 | 0 | 0 | 17.5 | 12.7 | Light Sediment |
| 21 | 0 | 0 | 0 | 2.5 | 0 | 0 | 17.5 | 12.7 | Solid |

Two weeks at −20° C.

| | | | | | | | | | |
|---|---|---|---|---|---|---|---|---|---|
| 22 | 2.5 | 0 | 0 | 0 | 0 | 0 | 20 | 10.2 | CB |
| 23 | 0 | 0 | 0 | 2.5 | 0 | 0 | 20 | 10.2 | Heavy Sediment |
| 24 | 10 | 0 | 0 | 0 | 0 | 10 | 0 | 12.7 | CB |
| 25 | 0 | 0 | 0 | 10 | 0 | 10 | 0 | 12.7 | Medium Sediment |
| 26 | 0 | 0 | 0 | 0 | 10 | 10 | 0 | 12.7 | Medium Sediment |
| 27 | 0 | 0 | 0 | 0 | 0 | 10 | 0 | 22.7 | Medium Sediment |

As shown in Table 6, the fuel additive concentrates that contain the composition 1 according to the invention (FAC Nos. 1, 9, and 15) remained clear and bright (CB) after four weeks at a temperature of −20° C. whereas the fuel additive concentrates containing Comparative compositions 1 and 2 (FAC Nos. 2, 3, 10, 11, 16 and 17) had heavy sediment after four weeks at −20° C.

Comparative composition 3 provided stable fuel additive concentrates that remained liquid at low temperature (FAC Nos. 4, 12, and 18). However, the fuel additive concentrates containing Comparative composition 3 and high levels of GMO or diethoxylated laurylamine became hazy within a week and unstable after two weeks (FAC Nos. 21, 23 and 25). Thus, the composition 1 according to the invention significantly improves the stability of fuel additive concentrates that would otherwise be unstable (FAC Nos. 7, 19, and 27) and allows the fuel additives to be used in concentrates that are stable at −20° C. (FAC Nos. 9, 20, and 24).

Comparative composition 4 is a mixture of alkanolamides made from coconut oil and methyl caprylate using the method disclosed in U.S. Pat. No. 6,524,353 B2. The use of methyl caprylate in the reaction mixture improves the low temperature performance of fuel additive product when it is blended into concentrates at 50% with aromatic solvent. However, the fuel additive concentrates that were made from Comparative composition 4 (FAC Nos. 5 and 26) were not stable at −20° C. when they were formulated with the fully formulated concentrates.

Accordingly, based on the foregoing stability tests, the fuel additive concentrates that are made with the composition 1 according to the invention had satisfactory stability at low temperature and the composition according to the invention may be used to improve the low temperature storage stability of a fuel additive composition that contains a fatty amine ethoxylate or GMO or both.

EXAMPLE 8: FUEL ECONOMY IMPROVEMENT OF THE COMPOSITION ACCORDING TO THE INVENTION

The composition according to the invention was evaluated for effectiveness in reducing fuel consumption in gasoline engines. The tests were conducted using the US Federal Test Procedure FTP-75 on chassis dynamometers under controlled temperature and humidity conditions while using the transient phase ("Bag 2") driving schedule in triplicate.

TABLE 7

Chassis Dynamometer Testing: Fuel Economy Increase

| Composition 1 according to the invention (ppm by wt.) | | % Fuel Economy Increase |
|---|---|---|
| 0 | Gasoline plus no top treat additive | 0 |
| 228 | 2010 Ford F150 4.6L/V8 | 0.71 |
| 342 | 2015 Volkswagen Golf 1.8L/DI | 0.84 |

As shown in the foregoing Table 7, the composition 1 according to the invention in a fuel additive composition at 228 and 342 ppm provided significant fuel economy increases compared to the base fuel composition that was devoid of the composition according to the invention.

Accordingly, in addition to friction and wear reduction and low temperature stability, the composition according to the invention also provides fuel economy improvements in gasoline fuels.

EXAMPLE 9

An engine test measuring fuel injector deposits (referred to as "DIG test") was performed following a procedure disclosed in SAE Int. J. Fuels Lubr. 10(3):2017 "A General Method for Fouling Injectors in Gasoline Direct Injection Vehicles and the Effects of Deposits on Vehicle Performance." A mathematical value of Long Term Fuel Trim (LTFT) was used to gauge the effectiveness of additives to clean up the injectors in a gasoline engine by running a dirty-up phase until the LTFT is 9-10% higher than at the start of test (approximately 6,000 miles) followed by a clean-up phase (approximately 2,000 miles). The lower the % LTFT at 8,000 miles, the more effective the additive is in cleaning up dirty injectors. For the DIG test, a 2012 Kia Optima (L-4, 2.4 L engine) equipped with a Direct Injection fuel management system was used. The composition 1 according to the invention was used at 67 ppm in a formulation that did not contain detergent. The results are shown in the following Table 8.

TABLE 8

| DIG Test: injector deposit clean-up | | | |
|---|---|---|---|
| Additive | Treat rate (ppm) | LTFT % after dirty-up | % Improvement after clean-up |
| Composition 1 according to the invention | 67 | 9.2 | 98 |

The composition according to the invention showed a significant clean-up of dirty injectors for a DIG engine at a relatively low treat rate.

The invention claimed is:

1. Composition comprising at least one fatty acid amide of diethanolamine (DEA) and from 15 to 80 wt. % of fatty acid ester(s) and/or amide(s) of DEA oligomer, with respect to the total weight of the composition.

2. The composition according to claim 1, wherein the at least one fatty acid amide of DEA is N,N-bis(2-hydroxyethyl)alkylamide.

3. The composition according to claim 1, wherein a fatty acid ester and/or amide of DEA oligomer is a fatty acid ester and/or amide of DEA dimer.

4. The composition according to claim 3, wherein the fatty acid ester of DEA dimer is 2-((2-(bis(2-hydroxyethyl)amino)ethyl)amino)ethylalkanoate.

5. The composition according to claim 3, wherein the fatty acid amide of DEA dimer is N-(2-(bis(2-hydroxyethyl)amino)ethyl)-N-(2-hydroxyethyl)alkylamide.

6. The composition according to claim 1, wherein a fatty acid ester and/or amide of DEA oligomer is a fatty acid ester and/or amide of DEA trimer.

7. The composition according to claim 3, wherein the quantity of fatty acid ester(s) of DEA dimer and fatty acid amide(s) of DEA dimer is comprised in the range from 15 to 50 wt. % with respect to the total weight of the composition.

8. The composition according to claim 1, wherein the quantity of fatty acid amide(s) of DEA is comprised in the range from 20 to 85 wt. % with respect to the total weight of the composition.

9. Process for preparing a composition according to claim 1, comprising reacting fatty acid(s) with DEA, wherein the reaction is conducted in the presence of a molar excess of DEA relative to the fatty acid(s) and at a pressure below 50000 Pa, and wherein the reaction is conducted at a temperature between 120 and 160° C., thereby preparing a composition comprising at least one fatty acid amide of DEA and from 15 to 80 wt. % of fatty acid ester(s) and/or amide(s) of DEA oligomer, with respect to the total weight of the composition.

10. The process according to claim 9, wherein the pressure is from 2000 to 50000 Pa.

11. The process according to claim 9, wherein the process comprises two steps:
a first step wherein the reaction is conducted at a pressure from above 5000 to 50000 Pa to obtain a reaction mixture, and,
once the reaction mixture reached an acid value of 50, a second step wherein the pressure is reduced to a pressure from 1000 to 5000 Pa.

12. The process according to claim 9, wherein fatty acid(s) is lauric acid, myristic acid, capric acid and/or caprylic acid.

13. The process according to claim 9, wherein the fatty acid(s) are fatty acids resulting from coconut oil.

14. The process according to claim 9, wherein the excess of DEA is removed after the reaction is completed.

* * * * *